(12) United States Patent
Quintanilha (10) Patent No.: US 9,632,424 B2
(45) Date of Patent: *Apr. 25, 2017

(54) ILLUMINATION SOURCE FOR USE IN INSPECTION METHODS AND/OR LITHOGRAPHY; INSPECTION AND LITHOGRAPHIC APPARATUS AND INSPECTION METHOD

(71) Applicant: ASML Netherlands B.V., Veldhoven (NL)

(72) Inventor: Richard Quintanilha, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 107 days.

This patent is subject to a terminal disclaimer.

(21) Appl. No.: 14/526,032

(22) Filed: Oct. 28, 2014

(65) Prior Publication Data

US 2015/0042999 A1     Feb. 12, 2015

Related U.S. Application Data (63) Continuation of application No. 13/490,414, filed on Jun. 6, 2012, now Pat. No. 8,876,346.

(Continued)

(51) Int. Cl.
*G02B 6/10* (2006.01)
*G03F 7/20* (2006.01)
(Continued)

(52) U.S. Cl.
CPC ....... *G03F 7/70191* (2013.01); *G01N 21/255* (2013.01); *G01N 21/47* (2013.01);
(Continued)

(58) Field of Classification Search
CPC  G02B 6/10; G02B 6/0008; G03F 7/20; G03F 7/70191; G03F 7/70058;
(Continued)

(56) References Cited

U.S. PATENT DOCUMENTS 4,535,394 A  *  8/1985  Dugre .............. F21V 9/08
                                                       362/231
4,677,473 A     6/1987  Okamoto et al.
(Continued)

FOREIGN PATENT DOCUMENTS

EP        1 628 164 A2    2/2006
WO    WO 2011/012624 A1   2/2011

OTHER PUBLICATIONS

Non-Final Rejection mailed Mar. 11, 2014 for U.S. Appl. No. 13/490,414, filed Jun. 6, 2012; 9 pages.
(Continued)

*Primary Examiner* — Bao Q Truong
(74) *Attorney, Agent, or Firm* — Sterne, Kessler, Goldstein & Fox P.L.L.C.

(57) ABSTRACT

An illumination system for a lithographic or inspection apparatus. A plurality of optical waveguides transmit radiation from the illumination source to an output. A switching system enables selective control of one or more subsets of the optical waveguides. An inspection method uses an illumination system and inspection and lithographic apparatuses comprise an illumination system. In one example, the optical waveguides and switching system are replaced by a plurality of parallel optical bandpass filter elements. The optical bandpass filter elements each only transmit a predetermined wavelength or a band of wavelengths of radiation. At least two of the parallel optical bandpass filter elements each being operable to transmit a different wavelength or band of wavelengths.

22 Claims, 7 Drawing Sheets

Related U.S. Application Data (60) Provisional application No. 61/512,555, filed on Jul. 28, 2011.

(51) Int. Cl.
   *G01N 21/47* (2006.01)
   *G01N 21/25* (2006.01)
   *F21V 8/00* (2006.01)

(52) U.S. Cl.
   CPC .............. *G02B 6/0008* (2013.01); *G02B 6/10* (2013.01); *G03F 7/20* (2013.01); *G03F 7/70058* (2013.01); *G01N 2201/062* (2013.01); *G01N 2201/06113* (2013.01); *G01N 2201/08* (2013.01)

(58) Field of Classification Search
   CPC ....... G01N 21/255; G01N 2201/06113; G01N 2201/08; G01N 21/47; G01N 2201/062; F21V 9/00; F21V 9/08; F21V 9/10; F21V 2200/10; F21V 2009/00; F21V 2009/08
   See application file for complete search history.

(56) References Cited

U.S. PATENT DOCUMENTS

| | | | |
|---|---|---|---|
| 4,894,760 A | 1/1990 | Callahan | |
| 5,302,999 A | 4/1994 | Oshida et al. | |
| 5,528,431 A * | 6/1996 | Wilkins | F21V 9/10 356/405 |
| 6,281,967 B1 * | 8/2001 | Kudo | G03F 7/70075 250/492.2 |
| 6,572,241 B1 * | 6/2003 | Chan | F21S 10/02 362/230 |
| 7,154,607 B2 | 12/2006 | Hendrix et al. | |
| 7,319,229 B2 | 1/2008 | Vaez-Iravani et al. | |
| 7,706,646 B2 | 4/2010 | Wang et al. | |
| 7,710,476 B2 * | 5/2010 | Nomura | H04N 9/045 348/273 |
| 8,721,123 B2 * | 5/2014 | Calmes | F21V 9/10 359/890 |
| 8,876,346 B2 * | 11/2014 | Quintanilha | G02B 6/10 362/551 |
| 8,885,150 B2 * | 11/2014 | Pellemans | G03F 7/70633 356/4.01 |
| 2008/0252868 A1 | 10/2008 | Chiu et al. | |
| 2010/0201963 A1 | 8/2010 | Cramer et al. | |
| 2012/0044470 A1 | 2/2012 | Smilde et al. | |
| 2013/0107226 A1 * | 5/2013 | Aksenov | H04N 9/315 353/31 |
| 2013/0141730 A1 | 6/2013 | Quintanilha | |

OTHER PUBLICATIONS

Notice of Allowance mailed Jul. 7, 2014 for U.S. Appl. No. 13/490,414, filed Jun. 6, 2012; 7 pages.

* cited by examiner

Fig. 9

ILLUMINATION SOURCE FOR USE IN INSPECTION METHODS AND/OR LITHOGRAPHY; INSPECTION AND LITHOGRAPHIC APPARATUS AND INSPECTION METHOD

This application incorporates by reference in their entireties U.S. patent application Ser. No. 13/490,414, filed Jun. 6, 2012 and U.S. provisional application 61/512,555, filed Jul. 28, 2011.

BACKGROUND

Field of the Invention

The present invention relates to methods and apparatus for lithography and/or metrology usable, for example, in the manufacture of devices by lithographic techniques and in particular to their illumination sources.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

Both lithography and scatterometry require an illumination source. In particular, scatterometry often requires a number of different illumination modes. The required illumination profiles for these illumination modes are usually obtained by the placing of a suitable aperture plate between the source and the target being measured. However, there can be many different illumination modes needed each requiring a different aperture plate. This ultimately puts a practical limit on the number of modes available. Additional flexibility can be obtained by using a Spatial Light Modulator (SLM). However, both aperture plates and SLMs reduce the amount of light available by ultimately blocking a portion of the light from the source.

SUMMARY

It is desirable to provide an illumination source that provides increased illumination control, while avoiding or at least mitigating one or more of the associated problems, mentioned above.

According to an embodiment of the present invention, there is provided an illumination system for a lithographic or inspection apparatus comprising an illumination source, a plurality of optical waveguides for transmitting radiation from the illumination source to an output, and a switching system enabling selective control of one or more subsets of the plurality of optical waveguides.

For the avoidance of doubt, a "subset" may comprise an individual waveguide, or may be a non-contiguous group of waveguides.

Another embodiment of the present invention provides an inspection apparatus and a lithographic apparatus comprising, for its primary illumination source, an illumination system as described above.

Another embodiment of the present invention provides an inspection method comprising directing a beam of radiation onto a target, the beam of radiation being obtained from an illumination system comprising: an illumination source, a plurality of optical waveguides for transmitting radiation from the illumination source to an output, and a switching system enabling selective control of one or more subsets of the plurality of optical waveguides, measuring one or more properties of the scattered radiation, and determining one or more properties of the target from the one or more measured properties of the scattered radiation.

According to a further embodiment of the present invention, there is provided an illumination system for a lithographic or inspection apparatus comprising an illumination source and an optical bandpass filter. The optical bandpass filter comprises a plurality of parallel optical bandpass filter elements. The optical bandpass filter elements each being operable to only transmit a predetermined wavelength or a band of wavelengths of radiation emitted by the illumination source. At least two of the parallel optical bandpass filter elements being operable to transmit different wavelengths or band of wavelengths.

According to a yet further embodiment of the present invention, there is provided an inspection method comprising obtaining a filtered beam of radiation by passing radiation through an optical bandpass filter, the optical bandpass filter comprising a plurality of different parallel optical bandpass filter elements, such that each optical bandpass filter element only transmits a different predetermined wavelength or band of wavelengths of radiation, directing the filtered beam of radiation onto a target, measuring one or more properties of the scattered radiation, and determining one or more properties of the target from the one or more measured properties of the scattered radiation.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

Embodiments of the invention will now be described, by way of example, with reference to the accompanying drawings in which:

FIG. 3 comprises (a) a schematic diagram of a dark field scatterometer for use in measuring targets according to embodiments of the invention, and (b) a detail of diffraction spectrum of a target grating for a given direction of illumination.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing embodiments of the invention in detail, it is instructive to present an example environment in which embodiments of the present invention may be implemented.

Figure 1:
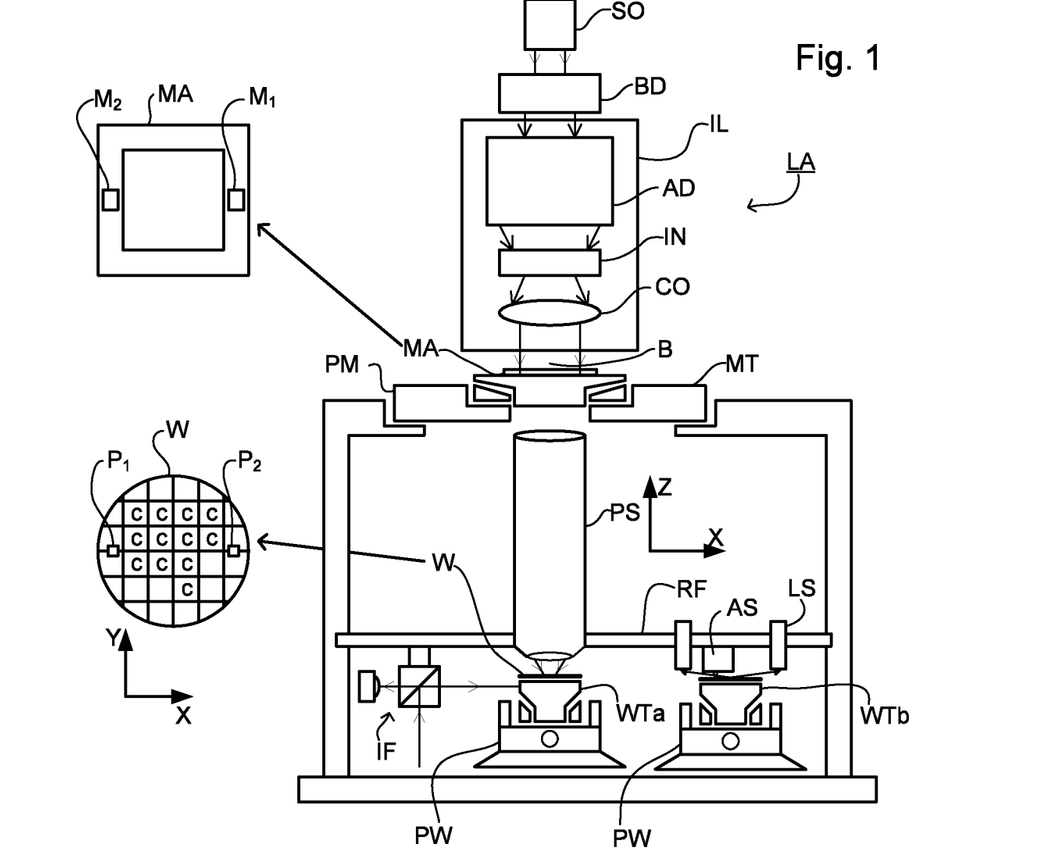
FIG. 1 depicts a lithographic apparatus according to an embodiment of the invention.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

The depicted apparatus could be used in at least one of the following modes:

1. In step mode, the patterning device support (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two substrate tables WTa, WTb and two stations—an exposure station and a measurement station— between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations.

Figure 2:
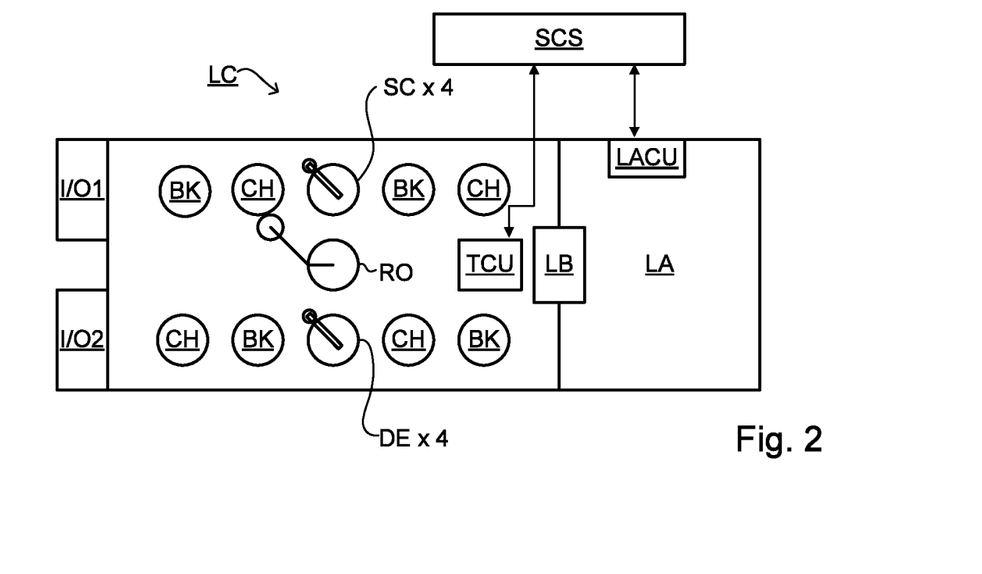
FIG. 2 depicts a lithographic cell or cluster according to an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

A metrology apparatus according to an embodiment of the invention is shown in FIG. 3(a). The apparatus shown is capable of performing so-called dark field metrology, where the zeroeth order is blocked. However, the invention may be used for other types of metrology apparatuses and techniques, as well as for lithographic apparatuses. A target grating T and diffracted rays are illustrated in more detail in FIG. 3(b).

The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done conventionally by inserting an aperture plate 13 of suitable form between lenses 12 and 14, in a plane which is a back-projected image of the objective lens pupil plane. Using, for example, an annular illumination profile, centered on the optical axis of the illumination system formed by lenses 12, 14 and 16, the measurement beam will be incident on substrate W in a cone of angles not encompassing the normal to the substrate. The illumination system thereby forms an off-axis illumination mode. Other modes of illumination are possible by using different apertures. The rest of the pupil plane is desirably dark as any unnecessary light outside the desired illumination mode will interfere with the desired measurement signals.

As shown in FIG. 3(b), target grating T is placed with substrate W normal to the optical axis O of objective lens 16. A ray of illumination I impinging on grating T from an angle off the axis O gives rise to a zeroeth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the annular aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

At least the 0 and +1 orders diffracted by the target on substrate W are collected by objective lens 16 and directed back through beam splitter 15. Remembering that, when using the illustrated annular aperture plate 13, incident rays I impinge on the target from a cone of directions rotationally symmetric about axis O, first order rays −1 from the opposite side of the cone will also enter the objective lens 16, even if the ray −1 shown in FIG. 3(b) would be outside the aperture of objective lens 16. Returning to FIG. 3(a), this is illustrated by designating diametrically opposite portions of the annular aperture as north (N) and south (S). The +1 diffracted rays from the north portion of the cone of illumination, which are labeled +1(N), enter the objective lens 16, and so do the −1 diffracted rays from the south portion of the cone (labeled −1(S)).

A second beam splitter 17 divides the diffracted beams into two measurement branches. In a first measurement branch, optical system 18 forms a diffraction spectrum (pupil plane image) of the target on first sensor using the zeroeth and first order diffractive beams. The sensor is preferably a two-dimensional sensor so that a two-dimensional angular scatter spectrum of a substrate target 30 can be measured. The sensor 19 may be, for example, an array of CCD or CMOS sensors, and may use an integration time of, for example, 40 milliseconds per frame. It is possible, in other embodiments, that this measurement branch images the structure itself, rather than the pupil plane.

Each diffraction order hits a different point on the sensor, so that image processing can compare and contrast orders. The sensor 19 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

The pupil plane image captured by sensor 19 can be used for focusing the metrology apparatus and/or normalizing intensity measurements of the first order beam. The pupil plane image can also be used for many measurement purposes such as reconstruction, where the structure or profile giving rise to the detected spectrum is reconstructed by processing unit PU, e.g. by Rigorous Coupled Wave Analysis and non-linear regression or by comparison with a library of simulated spectra. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

In the second measurement branch, optical system 20, 22 forms an image of the target on the substrate W on sensor 23 (e.g. a CCD or CMOS sensor). An aperture stop 21 is provided in a plane that is conjugate to the pupil-plane. Aperture stop 21 functions to block the zeroeth order diffracted beam so that the image of the target formed on sensor 23 is formed only from the first order beam. This is the so-called dark field image, equivalent to dark field microscopy. The images captured by sensors 19 and 23 are output to image processor and controller PU, the function of which will depend on the particular type of measurements being performed.

The target T on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

Using a broadband light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least 2 $\Delta\lambda$ (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporated by reference herein in its entirety.

Figure 3:
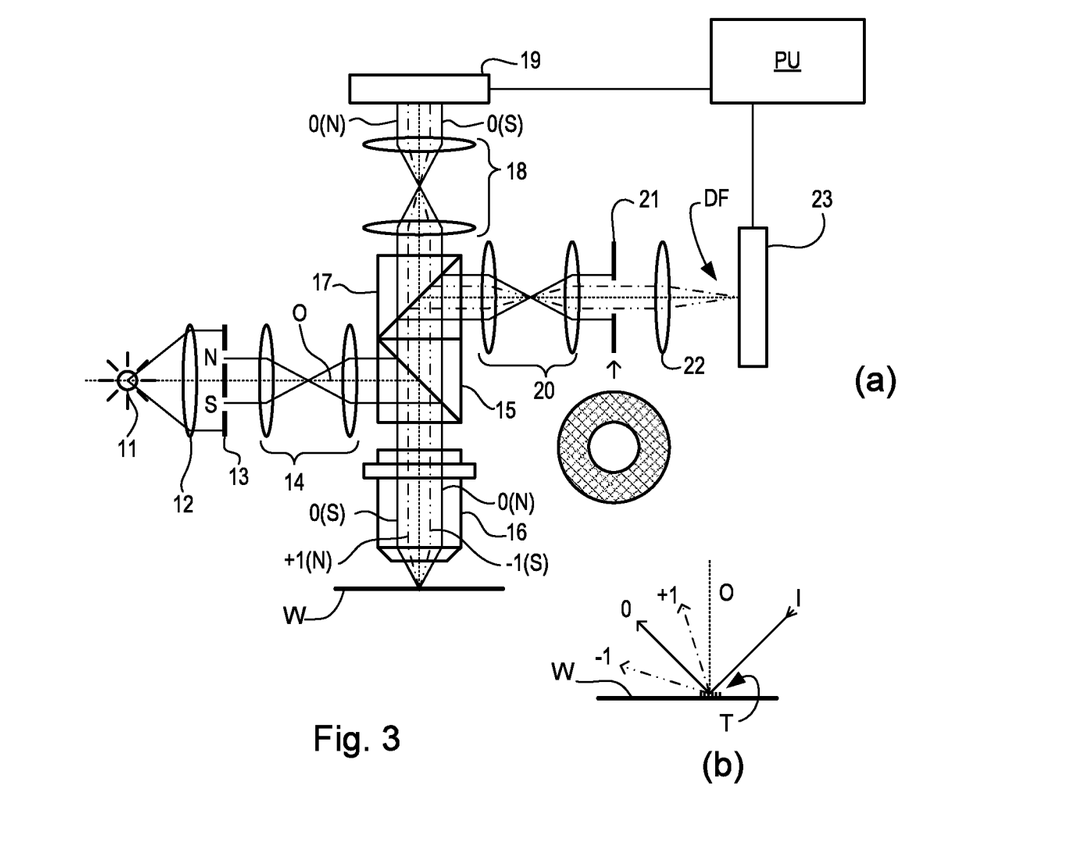

While off-axis illumination is shown, on-axis illumination of the targets may instead be used and an aperture stop with an off-axis aperture is used to pass substantially only one first order of diffracted light to the sensor. 2nd, 3rd and higher order beams (not shown in FIG. 3) can be used in measurements, instead of or in addition to the first order beams.

Figure 4:
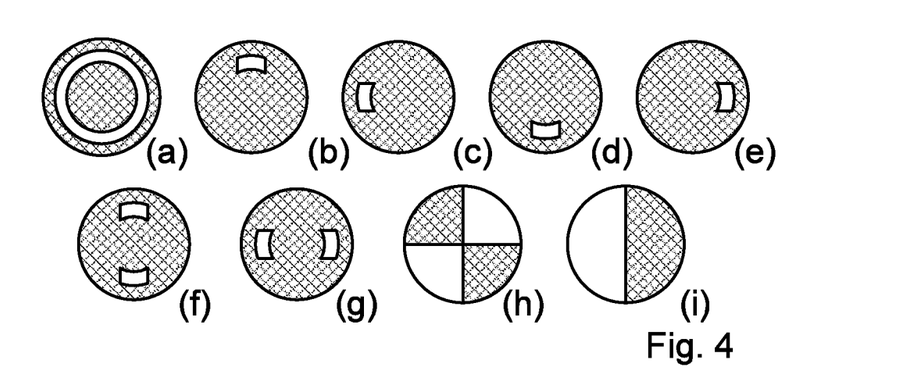
FIG. 4 shows a number of different illumination profiles useful for providing different illumination modes when using a scatterometer for diffraction based overlay measurements.

Illumination profiles can be varied greatly and the use of custom illumination is becoming more and more important in both lithography and optical metrology. The customization of the illumination enables improvement of the measurement quality (TMU, cross-correlation and sensitivity). Examples of some more commonly used illumination profiles are shown in FIG. 4. This shows annular illumination (a), unipolar illumination, which can admits light at certain angles around the optical axis only (b)-(e), bipolar illumination (f)-(g), opposite quadrant illumination (h) and half-field illumination (i). Unipolar illumination can be used to make asymmetry measurements of small target gratings, for the dark field overlay measurement method disclosed in international patent application PCT/EP2010/060894, incorporated herein by reference in its entirety. Illumination profiles (h) and (i), which allow separation of the zeroeth and first orders in the resultant image, are described in US patent publication 2010/0201963, incorporated herein by reference in its entirety.

All the optical systems used to control the illumination essentially customize the intensity (or the phase) across the pupil field. In the examples described thus far, specific apertures have been placed in the conjugate back focal plane (CBFP or illumination pupil plane) of the optical system. The use aperture plates provide customization at the expense of the amount of light transmitted, and are not always easy to implement for a general application. Some specific illuminations are for instance used for μDBO (micro-diffraction based overlay), but the aperture used in the CBFP is very specific while the number of different apertures must be limited, since the filter wheel has a finite number of slots. A Spatial Light Modulator (SLM) can be used as this provides more flexibility. However, this flexibility is at the expense of switch time, while the problem of the amount of light transmitted remains. Other specific systems for particular applications such as light homogenization have also been developed. However these systems are expensive and do not offer the flexibility needed in metrology.

Figure 5:
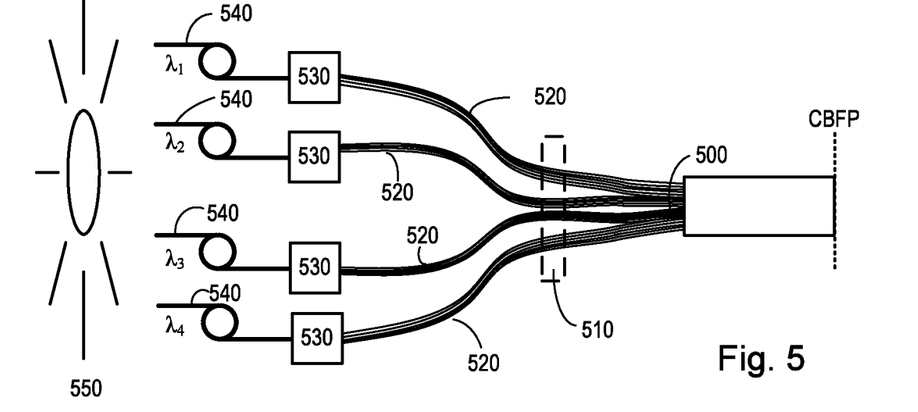
FIG. 5 shows a an illumination system according to an embodiment of the invention.

FIG. 5 shows a system which addresses the above issues. It shows a light source comprising a fiber bundle 500 placed in the CBFP. Fiber switches 510 are provided, to turn on and off (or partially off) each single fiber, thereby providing required flexibility in customizing the illumination. Multiples 520 of these fibers, grouped according to wavelength carried, are coupled via couplings 530 to a larger core (say 1 mm) fiber 540 at the source 550.

The source 550 used for the fiber bundle 500 can be a broadband lamp provided with a spectral filtering system, fiber coupled LEDs or fiber coupled Lasers. The design of the switching system 510 will depend on the number of fibers, the complexity of the main fiber bundle pattern and the source 550.

The number of fibers used in the fiber bundle 500 will essentially depend on the size of the fiber core chosen and the physical size of the CBFP of the instrument. Other factors which may influence the number of fibers in a bundle 500 are: the number of "angle of incidence" wanted, the output power of the fiber as a function of the core diameter and the feasibility of making an otherwise desirable fiber bundle 500. The fiber diameter also defines the angular resolution of the incident wave. It cannot be too small, otherwise diffraction effects will become paramount. In an illustrative example, if 200 μm core fibers are used and the CBFP diameter is 5 mm, the fiber bundle may be approximately made of 500 single fibers.

This illumination system makes it possible to set up different wavelengths for each fiber or set of fibers. Consequently it provides the capability to perform simultaneous measurements at different angles and wavelengths, and therefore spectroscopic and angle resolved measurement simultaneously in the pupil plane. This will improve the acquisition time of the experimental data. It will also improve the decorrelation of the parameters used in the reconstruction process, e.g. CD, n&k, thicknesses.

For example, measurement of the optical properties of a stack can be improved by using different wavelengths and angles to decorrelate the thickness of the layer from the optical properties of the layer. This can be done today using conventional scatterometry illumination sources. However, this requires a large number of measurements (one for each wavelength) to be taken. The illumination system described herein enables this to be done in a single measurement. In one particular example, where the structure studied has symmetry properties (e.g. a layered material or a zeroeth order grating), all four quadrants of the pupil plane will be identical for a single wavelength. Consequently, four wavelengths can be used in each quadrant simultaneously to extract more information of the target.

Figure 6A:
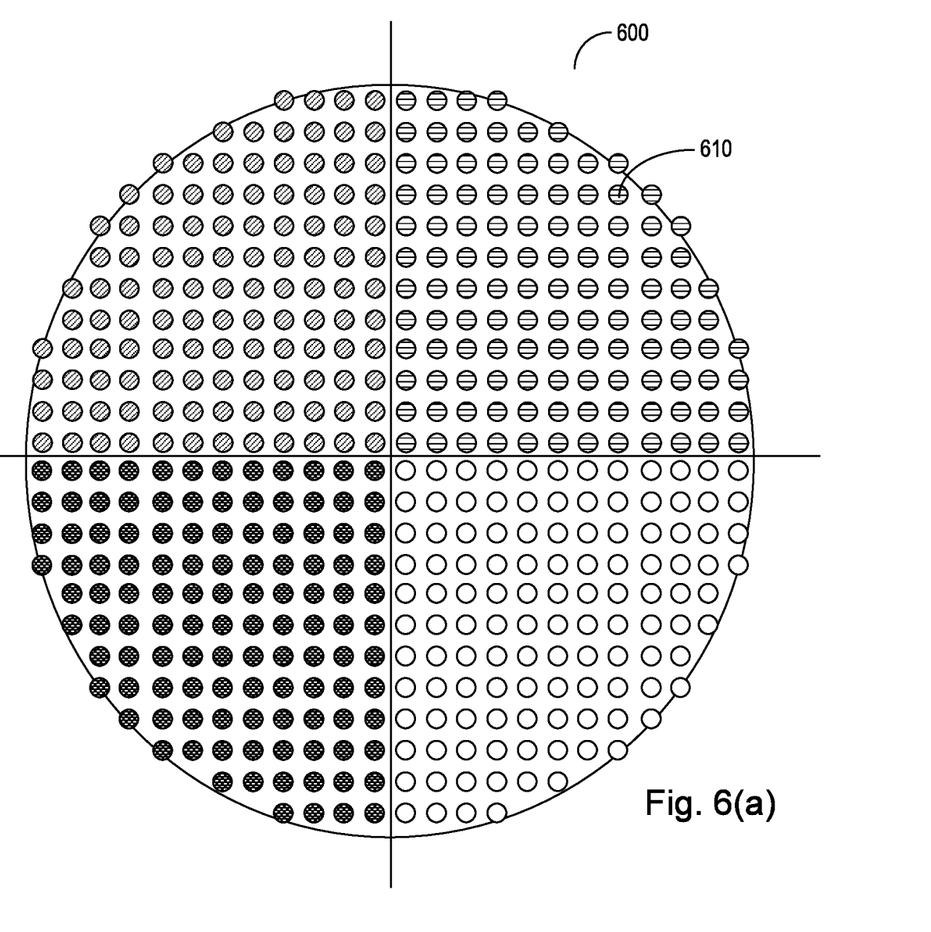
FIGS. 6(a) to 6(c) depicts three example illumination profiles possible using the apparatus of FIG. 5.
Figure 6B:
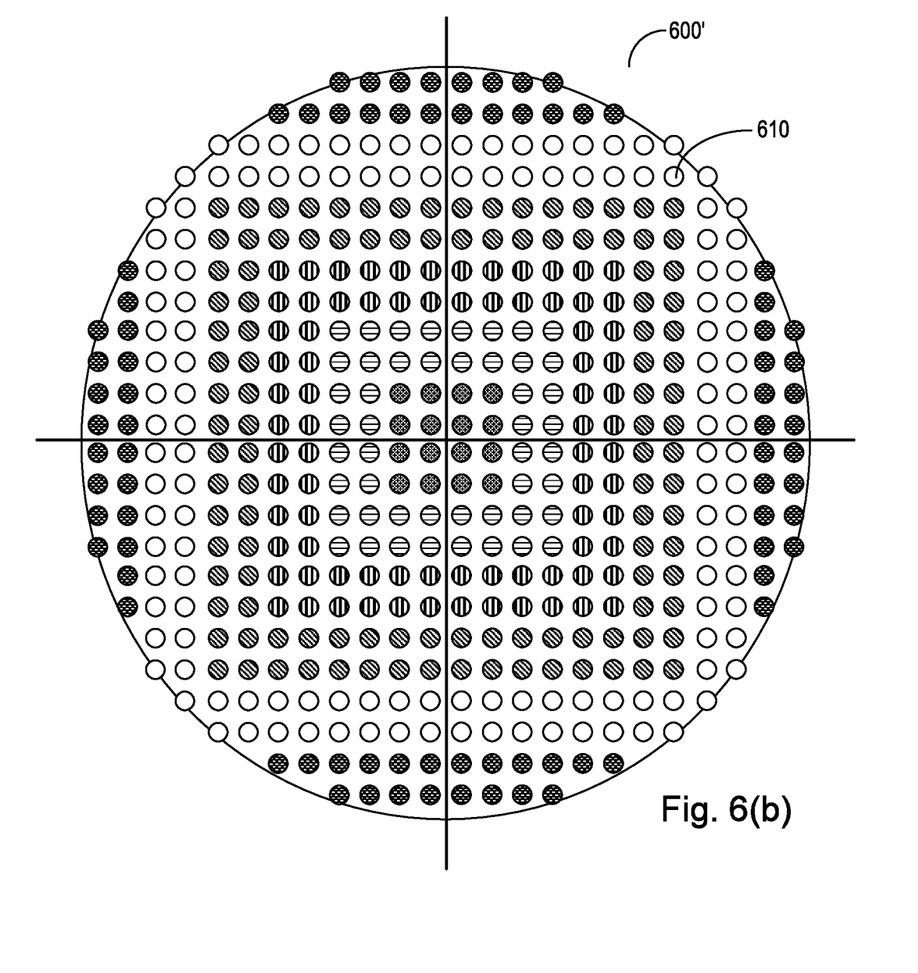
Figure 6C:
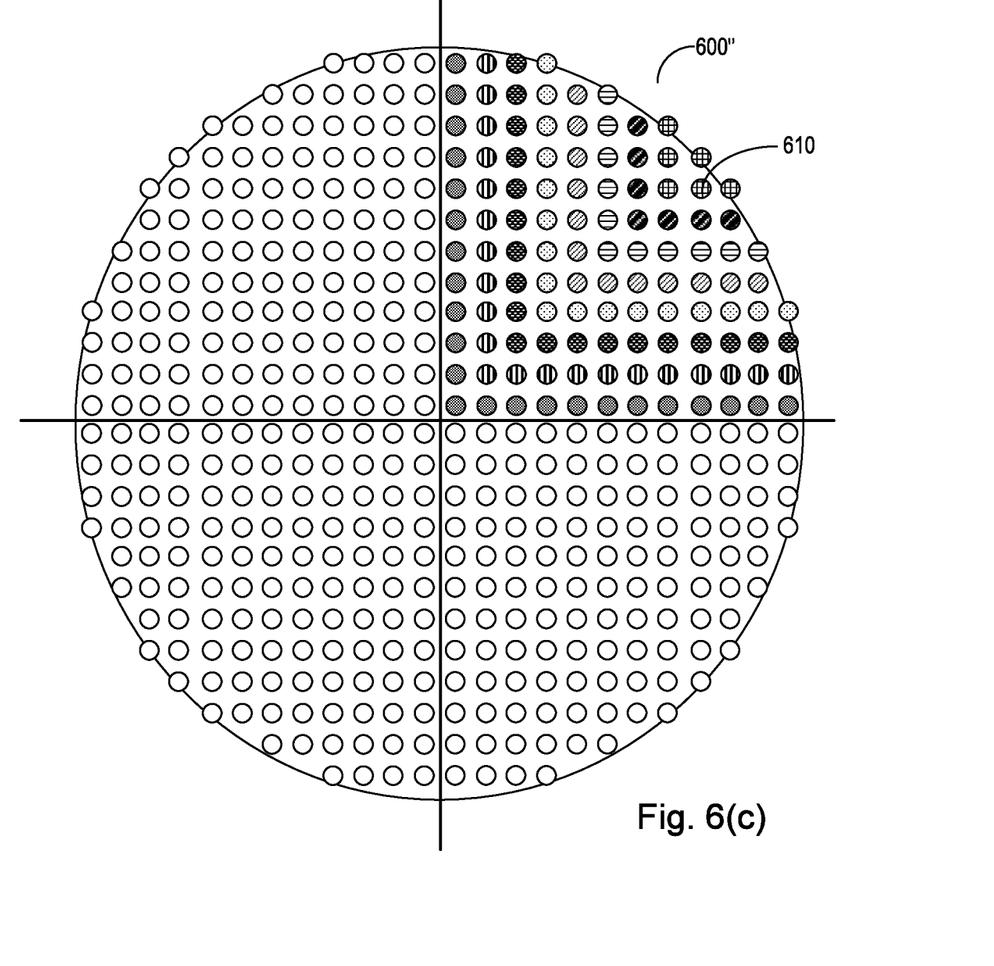

FIGS. 6(a) to 6(c) show some examples of possible wavelength and angle customization of the CBFP using an illumination system as described herein. Each figure shows an illumination profile 600, 600', 600" made up from individual fibers 610. Fibers carrying light of different wavelengths are differentiated by their hatching pattern. FIG. 6(a) shows an illumination profile 600 in which each quadrant has light of different wavelength. In FIG. 6(b), illumination profile 600' has light distributed such that regions of fibers having the same wavelength form concentric squares. In FIG. 6(c), illumination profile 600" has three quadrants with light of the same wavelength while the other quadrant has light of different wavelengths distributed such that regions of fibers having the same wavelength form nestled L-shapes. Of course, these examples are purely illustrative, and the number of different profiles is virtually limitless, and includes all those of FIG. 4.

It is also possible to customize the polarization of the CBFP by adding a custom polarizer. Such a custom polarizer may polarize each fiber or group of fibers differently. This means that it is possible to measure simultaneously two polarization states and two wavelengths for different angles of incidence. This reduces the acquisition time of the measurements (theoretically by a factor of four).

Figure 7:
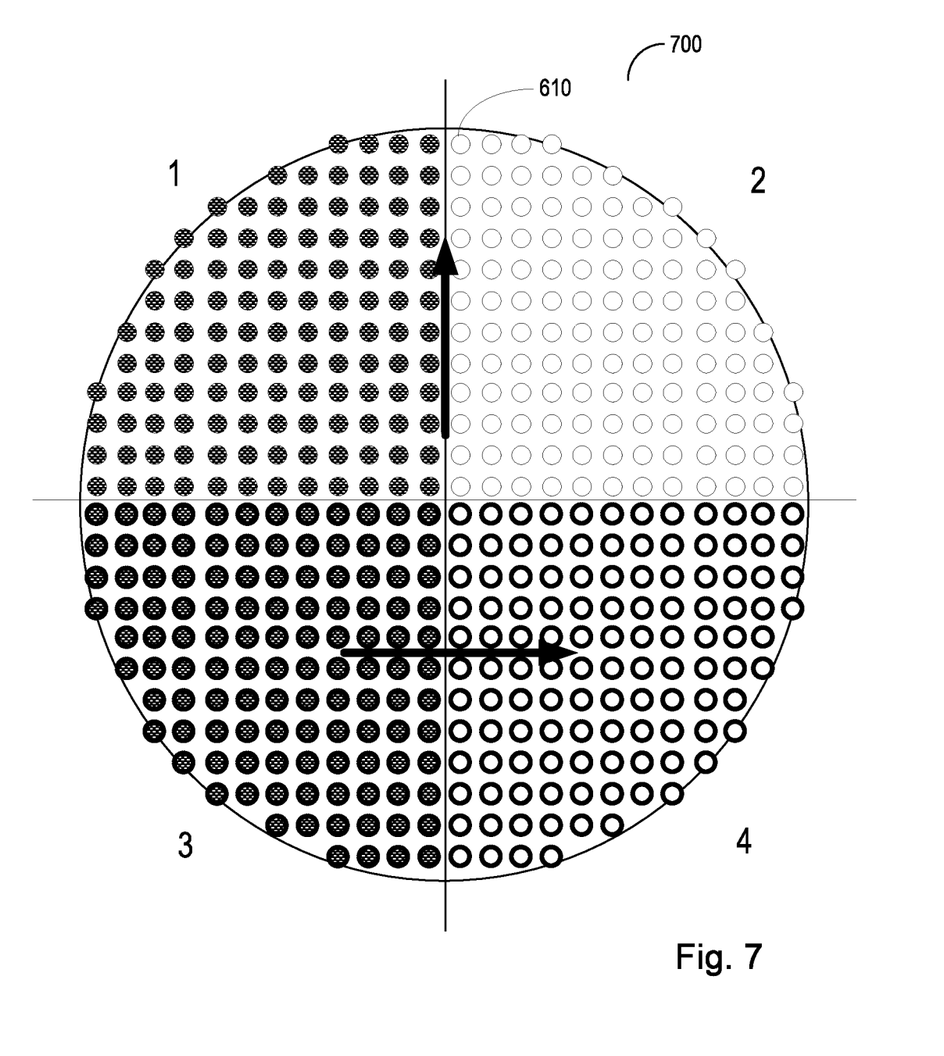
FIG. 7 shows an example illumination profiles possible using the apparatus of FIG. 5 with a custom polarizer.

FIG. 7 shows an example illumination profile 700 using a custom polarizer. Quadrants 1 and 2 are polarized in X (fibers 610 drawn with normal lines) and quadrants 3 and 4 are polarized in Y (fibers 610 drawn with bold lines). Also, quadrants 1 and 3 have a different wavelength to quadrants 2 and 4.

It is also possible to use polarization maintaining fibers and arrange them in a polar coordinate system to obtain a (p,s) polarization illumination, which will simplify the calibration and the simulation part of the inverse problem (the modeling of structures from the measured pupil spectra). Other arrangements are possible, so as to obtain the desired global polarization of the illumination. However, in these cases the fiber arrangement may be fixed. To change it will therefore require switching between fiber bundles.

It should also be noted that the illumination systems described above provide a good homogeneous (if the intensity of each fiber is the same) and incoherent source with a high radiance. Of course, as it is possible to customize the input intensity of each fiber, it is not only possible to make it homogenous but to provide for any other kind of intensity distribution.

One of the main advantages of the above illumination systems is that it allows the possibility of performing simultaneous measurements at different angles and wavelengths. However, it is sometimes desirable to keep any changes to the rest of the optical apparatus to a minimum. Consequently an embodiment has been devised, which replaces the fiber bundle arrangement with a optical bandpass filter arrangement.

Figure 8:
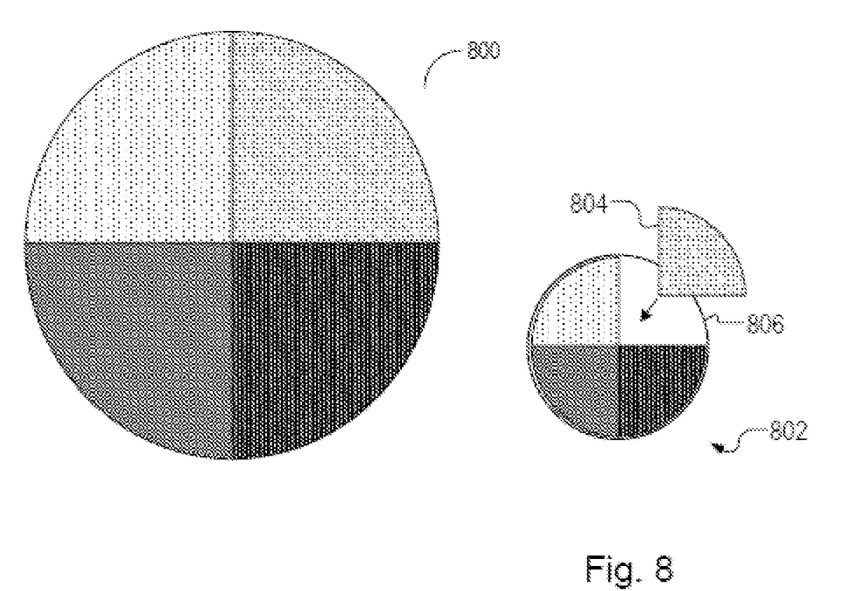
FIG. 8 shows an example illumination profiles possible using the apparatus of FIG. 5 with a custom polarizer.
Figure 9:
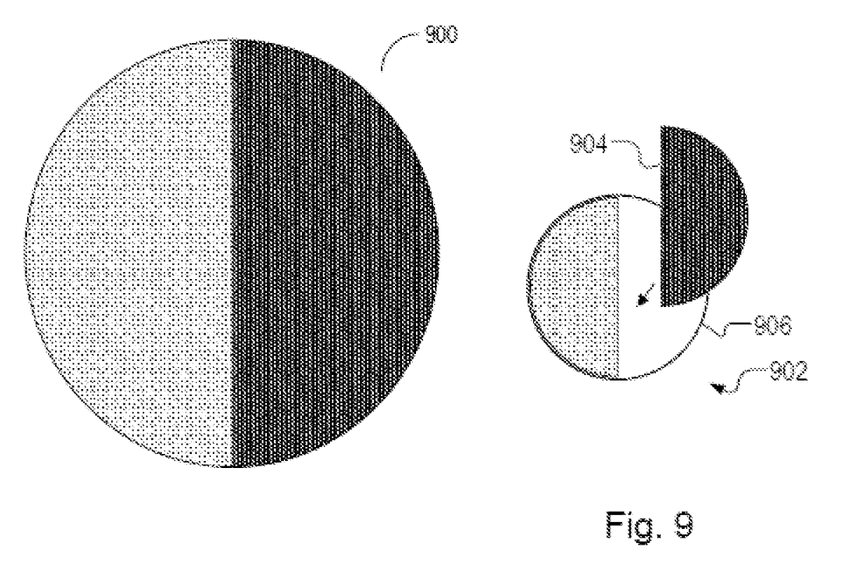
FIG. 9 shows an example illumination profiles possible using the apparatus of FIG. 5 with a custom polarizer.

FIG. 8 illustrates such an embodiment. Shown is an illumination profile 800 in which each of the four quadrants has a different wavelength (represented by different shading). FIG. 9 shows an alternative illumination profile 900 comprising two halves each having a different wavelength.

The illumination profile in this embodiment may be achieved by creating a custom optical band pass filter 802/902 that passes light of only certain wavelength(s), in each quarter (or other segment) of the pupil. The source of the tool should either be broadband, or have the desired multiple wavelengths. The wavelength filtering is performed in the CBFP using the custom bandpass filter.

Optical bandpass filters are usually square, rectangular or circular shaped. it is proposed that filter components 804/904 which make up the custom filter of this embodiment will be quarter-circle, half-circle or smaller circular shaped. These filter components may be mounted in a special mount 806/906, which will hold (for example) two or four of the filter components, depending on their shape and the desired illumination profile. Once fixed onto their mount, the custom filter can be placed on a rotating wheel in the pupil plane of the tool.

While specific embodiments of the invention have been described above, it will be appreciated that the invention may be practiced otherwise than as described. In association with the physical grating structures of the novel targets as realized on substrates and patterning devices, an embodiment may include a computer program containing one or more sequences of machine-readable instructions describing a methods of producing targets on a substrate, measuring targets on a substrate and/or analyzing measurements to obtain information about a lithographic process. This computer program may be executed for example within unit PU in the apparatus of FIG. 3 and/or the control unit LACU of FIG. 2. There may also be provided a data storage medium (e.g., semiconductor memory, magnetic or optical disk) having such a computer program stored therein.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultraviolet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A system comprising:
   a source of radiation;
   waveguides configured to transmit radiation from the source of radiation to an output;
   a switching system configured to allow selective control of transmission characteristics of the waveguides;
   a controller configured to select a wavelength of radiation output by the waveguides so as to define an illumination profile having different wavelengths simultaneously in different regions of an illumination pupil plane.

2. The system of claim 1, wherein the switching system is configured to switch between a transmitting state and a non-transmitting state of the waveguides.

3. The system of claim 1, wherein the controller is configured to select the wavelength of radiation output by each waveguide.

4. The system of claim 1, wherein the controller controls a filtering system between the source and the waveguides.

5. The system of claim 4, wherein the source of radiation comprises a broadband lamp.

6. The system of claim 1, wherein the controller directly controls the source of radiation.

7. The system of claim 6, wherein the source of radiation comprises fiber-coupled light emitting diodes.

8. The system of claim 1, wherein the controller is further configured to control polarization of radiation output by the waveguides.

9. The system of claim 8, wherein the controller is configured to individually control the polarization for each of the waveguides.

10. The system of claim 8, wherein at least some of the waveguides comprise polarization maintaining waveguides.

11. The system of claim 10, wherein the polarization maintaining waveguides are arranged in a polar coordinate system.

12. The system of claim 1, wherein the switching system is further configured to control whether each of the waveguides transmits, partially transmits, or does not transmit radiation to the output.

13. The system of claim 1, further comprising a sensor configured to detect the different wavelengths from the different regions of the illumination pupil plane.

14. A system comprising:
   a source of radiation;
   an optical bandpass filter comprising optical bandpass filter elements in parallel, wherein:
   the optical bandpass filter elements are operable to transmit a predetermined wavelength or a band of wavelengths of radiation emitted by the source of radiation,
   at least two of the optical bandpass filter elements are operable to transmit a different wavelength or band of wavelengths,
   wherein the predetermined wavelength or the band of wavelengths transmitted by each of the optical bandpass filter elements define an illumination profile that has different wavelengths simultaneously in different regions of an illumination pupil plane.

15. The system of claim 14, wherein the optical bandpass filter comprises four of the optical bandpass filter elements, each defining a quarter of the illumination profile.

16. The system of claim 14, wherein the optical bandpass filter comprises two of the optical bandpass filter elements, each defining a half of they illumination profile.

17. The system of claim 16, wherein the illumination profile is circular and each of the optical bandpass filter elements are quarter-circle shaped when numbering four, or half-circle shaped when numbering two.

18. The system of claim 14, wherein the optical bandpass filter comprises a mount for holding the optical bandpass filter elements in a desired configuration.

19. The system of claim 14, wherein the source of radiation comprises a broadband lamp.

20. The system of claim 14, further comprising a sensor configured to detect the different wavelengths or band of wavelengths from different regions of an illumination pupil plane.

21. The system of claim 1, wherein the illumination profile comprises a first region in the illumination pupil plane having only a first wavelength or set of wavelengths and a second region in the illumination pupil plane having only a second wavelength or set of wavelengths different from the first wavelength or set of wavelengths.

22. The system of claim 14, wherein the illumination profile comprises a first region in the illumination pupil plane having only a first wavelength or set of wavelengths and a second region in the illumination pupil plane having only a second wavelength or set of wavelengths different from the first wavelength or set of wavelengths.

\* \* \* \* \*